United States Patent
Wu

(10) Patent No.: US 12,390,613 B1
(45) Date of Patent: Aug. 19, 2025

(54) CONTROL METHOD, SYSTEM AND DEVICE FOR OXYGEN GENERATOR

(71) Applicant: Nanjing Mooxygen Medical Technology Co., Ltd., Nanjing (CN)

(72) Inventor: Ji Wu, Nanjing (CN)

(73) Assignee: Nanjing Mooxygen Medical Technology Co., Ltd., Nanjing (CN)

( * ) Notice: Subject to any disclaimer, the term of this patent is extended or adjusted under 35 U.S.C. 154(b) by 0 days.

(21) Appl. No.: 19/083,575

(22) Filed: Mar. 19, 2025

(30) Foreign Application Priority Data

Jul. 4, 2024 (CN) .................. 202410889024.0

(51) Int. Cl.
  *A61M 16/10* (2006.01)
  *A61M 16/20* (2006.01)
  *G16H 50/30* (2018.01)

(52) U.S. Cl.
  CPC ........ *A61M 16/101* (2014.02); *A61M 16/202* (2014.02); *G16H 50/30* (2018.01); *A61M 2230/06* (2013.01); *A61M 2230/205* (2013.01); *A61M 2230/42* (2013.01)

(58) Field of Classification Search
  CPC .............. A61M 16/101; A61M 16/026; A61M 16/024; B01D 2259/4533; G06N 20/00; G16H 40/60; A16H 50/20
  See application file for complete search history.

(56) References Cited

U.S. PATENT DOCUMENTS

| | | | |
|---|---|---|---|
| 2021/0322918 A1* | 10/2021 | Xiao | A61M 16/201 |
| 2023/0023722 A1* | 1/2023 | Warren | A61M 16/101 |
| 2023/0158268 A1* | 5/2023 | Navarro | A61M 16/101 |
| | | | 128/204.23 |

FOREIGN PATENT DOCUMENTS

| | | |
|---|---|---|
| CN | 211454313 U | 9/2020 |
| CN | 213581792 U | 6/2021 |
| CN | 113101478 A | 7/2021 |
| EP | 3960247 A | 3/2022 |
| WO | 2023116265 A1 | 6/2023 |

OTHER PUBLICATIONS

Notification to Grant Patent Right for Invention dated Sep. 6, 2024 in SIPO application No. 202410889024.0.
Retrieval report dated Aug. 9, 2024 in SIPO application No. 202410889024.0.

* cited by examiner

*Primary Examiner* — Margaret M Luarca
(74) *Attorney, Agent, or Firm* — Pilloff Passino & Cosenza LLP; Rachel K. Pilloff; Sean A. Passino

(57) ABSTRACT

A control method for an oxygen generator includes following steps: S101, performing S102 when the first physical sign data meets one of preset threshold conditions, otherwise performing S104; S102, switching the oxygen generator to a direct current oxygen outlet mode, and using the first model to output a first opening adjustment value of the direct current oxygen outlet solenoid valve; S103, adjusting an opening of the direct current oxygen outlet solenoid valve to the first opening adjustment value in the first preset time period B, S104, switching the oxygen generator to a pulse oxygen outlet mode; and S105, using a second model to output the second opening adjustment value when the pulse oxygen outlet solenoid valve is opened.

6 Claims, 6 Drawing Sheets

CONTROL METHOD, SYSTEM AND DEVICE FOR OXYGEN GENERATOR

CROSS-REFERENCE TO RELATED APPLICATIONS

This application claims priority of Chinese Patent Application No. 202410889024.0, filed on Jul. 4, 2024, the entire contents of which are incorporated herein by reference.

TECHNICAL FIELD

The present application belongs to the technical field of oxygen generator control, and in particular to a control method, a control system and a control device of the oxygen generator.

BACKGROUND

In the field of medical devices, the existing oxygen generators mainly include a direct current oxygen generator and a pulse oxygen generator. The direct current oxygen generator is based on PSA (molecular sieve pressure swing adsorption) technology, and usually adopts the working mode of double adsorption tower circulation, that is, in an adsorption tower, when air is compressed and passes through the molecular sieve, because the molecular sieve has stronger adsorption force on nitrogen and other gas molecules than oxygen, nitrogen is adsorbed by the molecular sieve, and oxygen passes through the molecular sieve to form high-concentration oxygen. At the same time, the other adsorption tower is in the stage of decompression and desorption, and the nitrogen adsorbed before is released by reducing the pressure or vacuumizing, thus completing the regeneration of the molecular sieve, and the two adsorption towers are periodically switched through the automatic control system to ensure the continuous supply of oxygen; the pulse oxygen generator is also based on PSA technology, but its difference from the direct current oxygen generator is that the direct current oxygen generator always provides oxygen at a constant speed, and the built-in sensor of the pulse oxygen generator may monitor the user's breathing pressure and breathing frequency, so that the user may accurately release oxygen when inhaling, and does not exhale oxygen when exhaling, thus improving the oxygen utilization rate.

However, the existing oxygen generators usually only have a single direct current oxygen generator or a single pulse oxygen generator, which fails to switch the oxygen outlet mode in real time according to the user's physical condition. For example, when the user has less active momentum or normal breathing, the pulse oxygen generator may improve the oxygen utilization rate, but when the user has more physical activities or abnormal breathing, the pulse oxygen generator may not provide enough oxygen in time, resulting in low breathing comfort and affecting safety of user.

SUMMARY

The application provides a control method, a system and a device for an oxygen generator, which solve the technical problems in the background technology.

The application provides a control method for an oxygen generator, including the following steps:

step S101, obtaining a first physical sign data of a user according to a first preset time interval A, performing step S102 when the first physical sign data meets one of preset threshold conditions, otherwise performing step S104;

where the first physical sign data includes: blood oxygen saturation, heart rate and breathing frequency;

step S102, switching the oxygen generator to a direct current oxygen outlet mode, and inputting the first physical sign data of the user into a first model, outputting a value as a first opening adjustment value of the direct current oxygen outlet solenoid valve in a first preset time period B;

step S103, adjusting an opening of the direct current oxygen outlet solenoid valve to the first opening adjustment value in the first preset time period B;

step S104, switching the oxygen generator to a pulse oxygen outlet mode, and obtaining a second physical sign data of the user according to a second preset time interval D in a second preset time period C to generate a feature sequence;

the feature sequence includes N sequence units, and an ith sequence unit represents the second physical sign data of the user at an ith time point, where $1 \leq i \leq N$ and $N=C/D$;

the second physical sign data includes: blood oxygen saturation, heart rate, breathing frequency and respiratory waveform graph;

a horizontal axis of respiratory waveform graph represents time point and a vertical axis represents airway pressure;

step S105, inputting the feature sequence into a second model, outputting a value as a second opening adjustment value when the pulse oxygen outlet solenoid valve is opened in a third preset time period E; and step S106, adjusting an opening of the pulse oxygen outlet solenoid valve to the second opening adjustment value in the third preset time period E.

Optionally, A, B, C, D and E are all self-defined parameters.

Optionally, preset threshold conditions include: the blood oxygen saturation is less than a first threshold; the heart rate is greater than or equal to a second threshold value; the breathing frequency is greater than or equal to ta third threshold; where the first threshold, the second threshold and the third threshold are all self-defined parameters.

Optionally, a calculation formula of the first model is as follows:

$$\text{Open} = \frac{1}{W_1} * \text{Blood}^\alpha + W_2 * \text{Heart}^\beta + W_3 * \text{Breath}^\gamma,$$

where $\text{Open}_1$ represents the first opening adjustment value, Blood, Heart and Breath respectively represent blood oxygen saturation, heart rate and breathing frequency; $W_1$, $W_2$ and $W_3$ respectively represent a first weight parameter, a second weight parameter and a third weight parameter, $\alpha$, $\beta$, and $\gamma$ respectively represent first, second and third influence coefficients.

Optionally, the first model is fitted by least square method, and a mean square error is designated as the loss function of the first model. The weight parameters and influence coefficients of the first model are updated by gradient descent algorithm to minimize the loss function of the first model, in which the first opening adjustment value of a training sample used for fitting the first model is set by evaluating of relevant technical experts.

Optionally, the pulse oxygen outlet solenoid valve is opened at a corresponding time point at a peak of the respiratory waveform graph, and the pulse oxygen outlet solenoid valve is closed at a corresponding time point at a trough of the respiratory waveform graph.

Optionally, the second model includes N hidden layers, an ith hidden layer inputs the ith sequence unit of the feature sequence and outputs a hidden state;

the hidden state output by an Nth hidden layer is input into a classifier, and the classification space of the classifier represents the second opening adjustment value when the pulse oxygen outlet solenoid valve is opened in the third preset time period E;

a calculation formula of the second model includes:

$$r_i = \text{ReLU}(W_i^{r,1} * x_i + W_i^{r,2} * h_{i-1} + b_i^r),$$
$$z_i = \text{ReLU}(W_i^{z,1} * x_i + W_i^{z,2} * h_{i-1} + b_i^z),$$
$$\tilde{h}_1 = \tanh(W_i^{h,1} * x_i + (r_i \odot h_{i-1}) * W_i^{h,2} + b_i^h),$$
$$h_i = z_i \odot h_{i-1} + (1 - z_i) \odot \tilde{h}_1,$$

where $X_i$ represents the ith sequence unit of the feature sequence input by the ith hidden layer, and $h_i$ and $h_{i-1}$ respectively represent hidden state output by the ith hidden layer and the i-1th hidden layer, $h_0$ is assigned as 0, $r_i$, $z_i$ and $\tilde{h}_1$, respectively represent reset gate, update gate and candidate hidden state of the ith hidden layer, $W_i^{r,1}$, $W_i^{r,2}$ and and $b_i^r$ respectively represent the first weight parameter, second weight parameter and offset parameter corresponding to the reset gate of the ith hidden layer, $W_i^{z,1}$, $W_i^{z,2}$ and $b_i^z$ respectively represent the first weight parameter, second weight parameter and offset parameter corresponding to the update gate of the ith hidden layer, $W_i^{h,1}$, $W_i^{z,2}$, and $b_i^h$ respectively represent the first weight parameter, the second weight parameter and the offset parameter corresponding to the candidate hidden state of the ith hidden layer, $\odot$ represents Hadamard product, ReLU represents ReLU activation function, and tanh represents hyperbolic tangent activation function.

Optionally, obtaining a sample label of the training sample for training the second model includes following steps:

step S301, before using the oxygen generator, self-defining standard values of blood oxygen saturation, heart rate and breathing frequency of the user as a first vector;

step S302, randomly generating one opening value as a second opening adjustment value when the pulse oxygen outlet solenoid valve is opened in the third preset time period E;

step S303, after the third preset time period E, measuring the blood oxygen saturation, heart rate and breathing frequency of the user as a second vector, and calculating a Euclidean distance between the first vector and the second vector;

step S304, repeating step S301 to step S303 to obtain a second opening adjustment value corresponding to a minimum value of the Euclidean distance between the first vector and the second vector as the sample label of the training sample; and step S305, repeating step S304 until sample labels of K training samples are obtained, where K is a self-defined parameter.

The application provides a control system of an oxygen generator, including:

a direct current oxygen outlet mode switching module, used for acquiring the first physical sign data of the user according to the first preset time interval A, and switching the oxygen generator to the direct current oxygen outlet mode when the first physical sign data meets one of the preset threshold conditions;

a first opening adjustment value prediction module, used to input the first physical sign data of the user into a first model, to output a value as the first opening adjustment value of the direct current oxygen outlet solenoid valve in a first preset time period B;

a direct current oxygen outlet solenoid valve adjusting module, used for adjusting the opening of the direct current oxygen outlet solenoid valve to a first opening adjustment value in a first preset time period B;

a pulse oxygen outlet mode switching module, used for acquiring the first physical sign data of the user according to the first preset time interval A, and switching the oxygen generator to the pulse oxygen outlet mode when the first physical sign data does not meet any of the preset threshold conditions;

a second opening adjustment value prediction module, used for acquiring the second physical sign data of the user in a second preset time period C according to a second preset time interval D, generating a feature sequence, inputting the feature sequence into a second model, outputting a value as the second opening adjustment value when the pulse oxygen outlet solenoid valve is opened in a third preset time period E;

a pulse oxygen outlet solenoid valve adjusting module, used for adjusting the opening of the pulse oxygen outlet solenoid valve to a second opening adjustment value in a third preset time period E.

The application provides a control device of an oxygen generator, including:

an inflating device, first solenoid valve, second solenoid valve, first sieve bucket, first oxygen bridge, third solenoid valve, second sieve bucket, first one-way valve, second one-way valve, gas storage tank, second oxygen bridge, pulse valve, direct current valve and oxygen outlet nozzle;

where the inflating device is respectively connected with the first solenoid valve and the second solenoid valve through pipelines, the first sieve bucket is respectively connected with the first solenoid valve, the first oxygen bridge and the first one-way valve through pipelines, the second sieve bucket is respectively connected with the second one-way valve, the third solenoid valve and the second one-way valve through pipelines, the third solenoid valve is connected with the first oxygen bridge through pipelines, and the gas storage tank is respectively connected with the first one-way valve, the second one-way valve, the pulse valve and the second oxygen bridge through pipelines, and the second oxygen bridge and the direct current valve are connected through pipelines, and the oxygen outlet nozzle is respectively connected with pulse valve and direct current valve through pipeline.

The application has the beneficial effects that the direct current oxygen outlet and the pulse oxygen outlet are integrated into one oxygen generator, and the oxygen outlet mode is switched in real time according to the user's physical sign data, and the nonlinear mapping relationship between the opening adjustment values of the direct current solenoid valve and the pulse solenoid valve and the user's physical sign data is established through the first model and the second model respectively, thus improving the oxygen utilization rate while ensuring the user's breathing comfort.

DETAILED DESCRIPTION OF THE EMBODIMENTS

Figure 1:
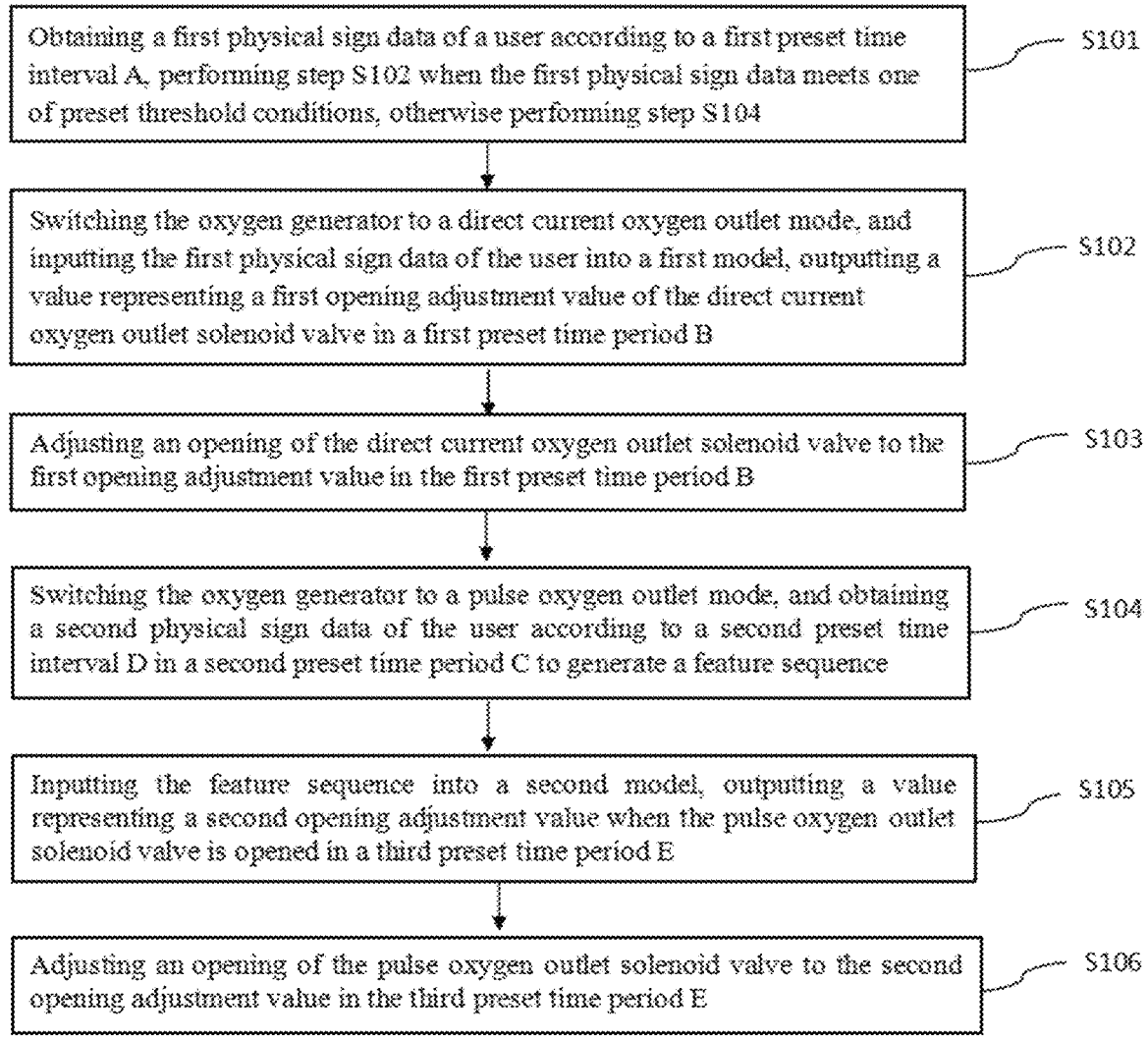
FIG. 1 is a flow chart of a control method of an oxygen generator of the present application.

The subject matter described herein will now be discussed with reference to example embodiments. It should be understood that these embodiments are discussed only to enable those skilled in the art to better understand and realize the subject matter described herein, and the functions and arrangements of the discussed elements can be changed without departing from the scope of protection of this specification. Each embodiment can omit, replace or add various processes or components as needed. In addition, features described with respect to some examples can also be combined in other examples.

It should be noted that, unless otherwise defined, technical terms or scientific terms used in one or more embodiments of the present application should have their ordinary meanings as understood by people with ordinary skills in the field to which the present application belongs. The terms "first", "second" and the like used in one or more embodiments of the present application do not indicate any order, quantity or importance, but are only used to distinguish different components. Similar words such as "including" or "containing" mean that the elements or objects appearing before the word cover the elements or objects listed after the word and their equivalents, without excluding that other elements or objects are "connected" or "mutually connected" and similar words are not limited to physical or mechanical connections, but may include electrical connections, whether direct or indirect. "Up", "Down", "Left" and "Right" are only used to indicate the relative positional relationship. When the absolute position of the described object changes, the relative positional relationship may also change accordingly.

As shown in FIG. 1-FIG. 6, a control method for an oxygen generator includes the following steps:

step S101, obtaining a first physical sign data of a user according to a first preset time interval A, performing step S102 when the first physical sign data meets one of preset threshold conditions, otherwise performing step S104;

where the first physical sign data includes: blood oxygen saturation, heart rate and breathing frequency;

step S102, switching the oxygen generator to a direct current oxygen outlet mode, and inputting the first physical sign data of the user into a first model, outputting a value as a first opening adjustment value of the direct current oxygen outlet solenoid valve in a first preset time period B;

step S103, adjusting an opening of the direct current oxygen outlet solenoid valve to the first opening adjustment value in the first preset time period B;

step S104, switching the oxygen generator to a pulse oxygen outlet mode, and obtaining a second physical sign data of the user according to a second preset time interval D in a second preset time period C to generate a feature sequence;

the feature sequence includes N sequence units, and an ith sequence unit represents the second physical sign data of the user at an ith time point, where $1 \leq i \leq N$ and $N=C/D$;

the second physical sign data includes: blood oxygen saturation, heart rate, breathing frequency and respiratory waveform graph;

a horizontal axis of respiratory waveform graph represents time point and a vertical axis represents airway pressure;

step S105, inputting the feature sequence into a second model, outputting a value as a second opening adjustment value when the pulse oxygen outlet solenoid valve is opened in a third preset time period E; and step S106, adjusting an opening of the pulse oxygen outlet solenoid valve to the second opening adjustment value in the third preset time period E.

In an embodiment of the present application, A, β, C, D and E are all self-defined parameters. Preferably, A is set to 1 minute, B is set to 5 minutes, C is set to 1 minute, D is set to 5 seconds, then N is 12 and E is set to 2 minutes.

In an embodiment of the present application, the user's blood oxygen saturation is obtained by a pulse oximeter, the user's heart rate is obtained by a portable heart rate detector, the user's breathing frequency is obtained by a breathing frequency detector, and the user's respiratory waveform graph is obtained by a breathing mechanics monitor.

In an embodiment of the present application, preset threshold conditions include: the blood oxygen saturation is less than a first threshold; the heart rate is greater than or equal to a second threshold value; the breathing frequency is greater than or equal to ta third threshold; where the first threshold, the second threshold and the third threshold are all self-defined parameters and specifically, they are evaluated and set by relevant technical experts.

In an embodiment of the present application, a calculation formula of the first model is as follows:

$$\text{Open}_1 = \frac{1}{W_1} * \text{Blood}^\alpha + W_2 * \text{Heart}^\beta + W_3 * \text{Breath}^\gamma,$$

where $\text{Open}_1$ represents the first opening adjustment value, Blood, Heart and Breath respectively represent blood oxygen saturation, heart rate and breathing frequency; $W_1$, $W_2$ and $W_3$ respectively represent a first weight parameter, a second weight parameter and a third weight parameter, α, β, and γ respectively represent first, second and third influence coefficients.

In an embodiment of the present application, the first model is fitted by least square method, and a mean square error is designated as the loss function of the first model. The weight parameters and influence coefficients of the first model are updated by gradient descent algorithm to minimize the loss function of the first model, in which the first opening adjustment value of a training sample used for fitting the first model is set by evaluating of relevant technical experts.

In an embodiment of the present application, the pulse oxygen outlet solenoid valve is opened at a corresponding time point at a peak of the respiratory waveform graph, and the pulse oxygen outlet solenoid valve is closed at a corresponding time point at a trough of the respiratory waveform graph.

Figure 2:
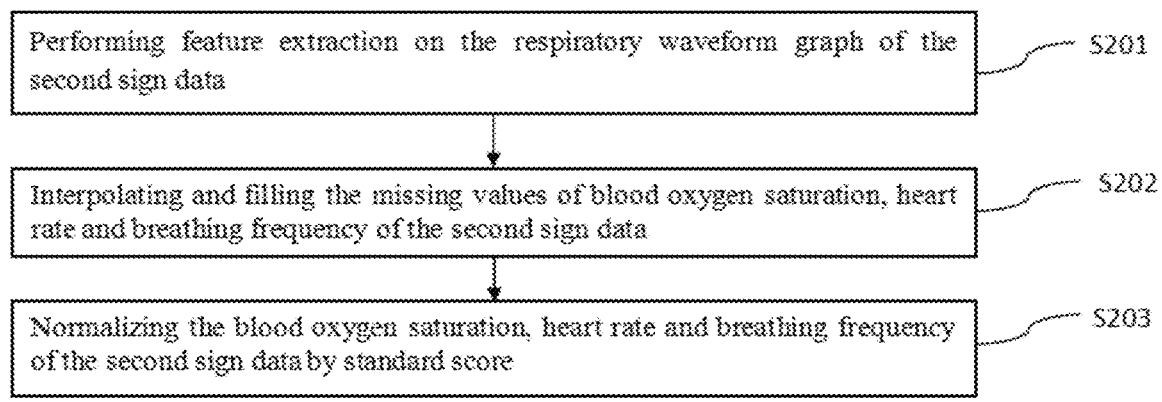
FIG. 2 is a flow chart of preprocessing the second physical sign data of the present application.

In an embodiment of the present application, as shown in FIG. 2, before generating the feature sequence, the second physical sign data may be preprocessed, including the following steps:

step S201, performing feature extraction on the respiratory waveform graph of the second physical sign data, including the number of peaks, the number of troughs and the average time difference between peaks and troughs;

step S202, interpolating and filling the missing values of blood oxygen saturation, heart rate and breathing frequency of the second physical sign data, that is, taking the average value of the data of the two closest time points corresponding to the missing value for filling;

step S203, normalizing the blood oxygen saturation, heart rate and breathing frequency of the second physical sign data by z-score (standard score).

In an embodiment of the present application, the second model includes N hidden layers, an ith hidden layer inputs the ith sequence unit of the feature sequence and outputs a hidden state;

the hidden state output by an Nth hidden layer is input into a classifier, and the classification space of the classifier represents the second opening adjustment value when the pulse oxygen outlet solenoid valve is opened in the third preset time period E;

a calculation formula of the second model includes:

$$r_i = \text{ReLU}(W_i^{r,1} * x_i + W_i^{r,2} * h_{i-1} + b_i^r),$$

$$z_i = \text{ReLU}(W_i^{z,1} * x_i + W_i^{z,2} * h_{i-1} + b_i^z),$$

$$\tilde{h}_1 = \tanh(W_i^{h,1} * x_i + (r_i \odot h_{i-1}) * W_i^{h,2} + b_i^h),$$

$$h_i = z_i \odot h_{i-1} + (1 - z_i) \odot \tilde{h}_1,$$

where $x_i$ represents the ith sequence unit of the feature sequence input by the ith hidden layer, and $h_i$ and $h_{i-1}$ respectively represent hidden state output by the ith hidden layer and the i-1th hidden layer, $h_0$ is assigned as 0, $r_i$, $z_i$ and $\tilde{h}_1$, respectively represent reset gate, update gate and candidate hidden state of the ith hidden layer, $W_i^r$, $W_i^{r,2}$ and $b_i^r$ respectively represent the first weight parameter, second weight parameter and offset parameter corresponding to the reset gate of the ith hidden layer, $W_i^{z,1}$, $W_i^{z,2}$ and $b_i^z$ respectively represent the first weight parameter, second weight parameter and offset parameter corresponding to the update gate of the ith hidden layer, $W_i^{h,1}$, $W_i^{h,2}$ and $b_i^h$ respectively represent the first weight parameter, the second weight parameter and the offset parameter corresponding to the candidate hidden state of the ith hidden layer, @ represents Hadamard product, ReLU represents ReLU activation function, and tanh represents hyperbolic tangent activation function.

Figure 3:
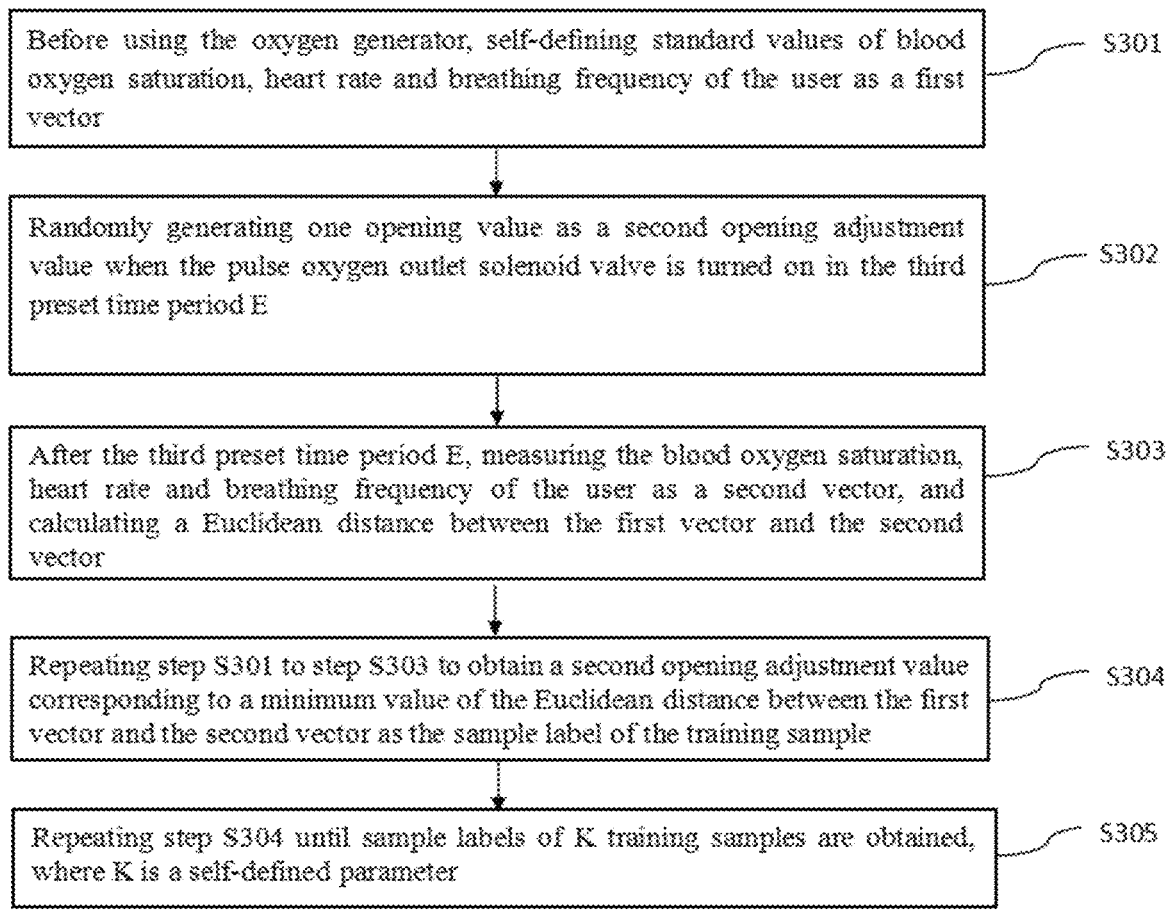
FIG. 3 is a flow chart of the present application for obtaining a sample label of a training sample for training a second model.

In an embodiment of the present application, as shown in FIG. 3, obtaining a sample label of the training sample for training the second model includes following steps:

step S301, before using the oxygen generator, self-defining standard values of blood oxygen saturation, heart rate and breathing frequency of the user as a first vector, where the standard values of blood oxygen saturation, heart rate and breathing frequency are set by relevant technical experts according to the physical condition of the user;

step S302, randomly generating one opening value as a second opening adjustment value when the pulse oxygen outlet solenoid valve is opened in the third preset time period E;

step S303, after the third preset time period E, measuring the blood oxygen saturation, heart rate and breathing frequency of the user as a second vector, and calculating a Euclidean distance between the first vector and the second vector;

step S304, repeating step S301 to step S303 to obtain a second opening adjustment value corresponding to a minimum value of the Euclidean distance between the first vector and the second vector as the sample label of the training sample; and step S305, repeating step S304 until sample labels of K training samples are obtained, where K is a self-defined parameter and preferably K is set to 2000.

In an embodiment of the present application, after the third preset time period E, the user's respiratory comfort can also be collected as a sample label of a training sample through questionnaire survey, and the range of respiratory comfort can be set between 0 and 10.

In an embodiment of the present application, the difference between the output value of the second model in each iteration and the sample label of the training sample is designated as the loss function, the gradient information of the weight parameters and offset parameters of the second model is calculated by the back propagation algorithm, and then the weight parameters and offset parameters are updated by the gradient descent algorithm according to the gradient information, so that the loss function of the second model is minimized.

Figure 4:
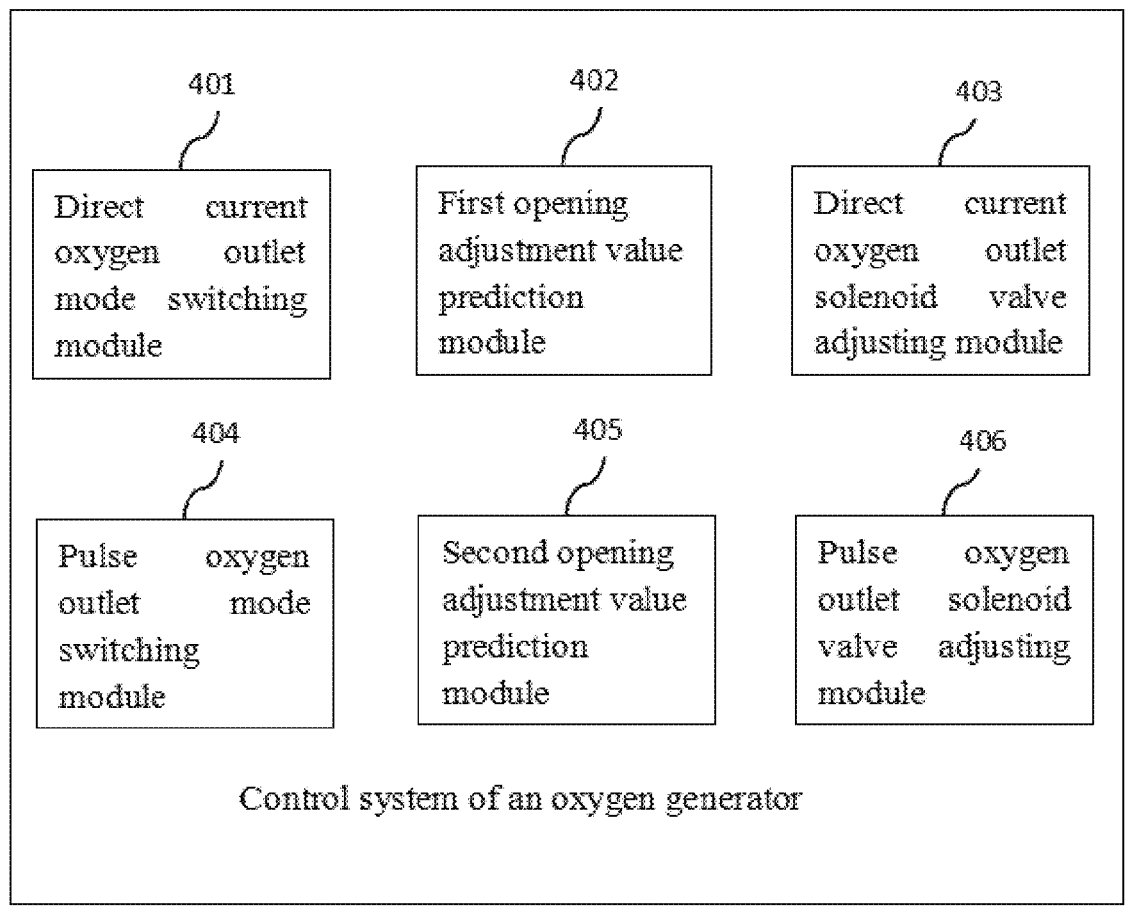
FIG. 4 is a schematic diagram of the control system of an oxygen generator of the present application.

As shown in FIG. 4, the present application provides a control system of an oxygen generator, including:

a direct current oxygen outlet mode switching module 401, used for acquiring the first physical sign data of the user according to the first preset time interval A, and switching the oxygen generator to the direct current oxygen outlet mode when the first physical sign data meets one of the preset threshold conditions;

a first opening adjustment value prediction module 402, used to input the first physical sign data of the user into a first model, to output a value as the first opening adjustment value of the direct current oxygen outlet solenoid valve in a first preset time period B;

a direct current oxygen outlet solenoid valve adjusting module 403, used for adjusting the opening of the direct current oxygen outlet solenoid valve to a first opening adjustment value in a first preset time period B;

a pulse oxygen outlet mode switching module 404, used for acquiring the first physical sign data of the user according to the first preset time interval A, and switching the oxygen generator to the pulse oxygen outlet mode when the first physical sign data does not meet any of the preset threshold conditions;

a second opening adjustment value prediction module 405, used for acquiring the second physical sign data of the user in a second preset time period C according to a second preset time interval D, generating a feature sequence, inputting the feature sequence into a second model, outputting a value as the second opening adjustment value when the pulse oxygen outlet solenoid valve is opened in a third preset time period E;

a pulse oxygen outlet solenoid valve adjusting module 406, used for adjusting the opening of the pulse oxygen outlet solenoid valve to a second opening adjustment value in a third preset time period E.

Figure 5:
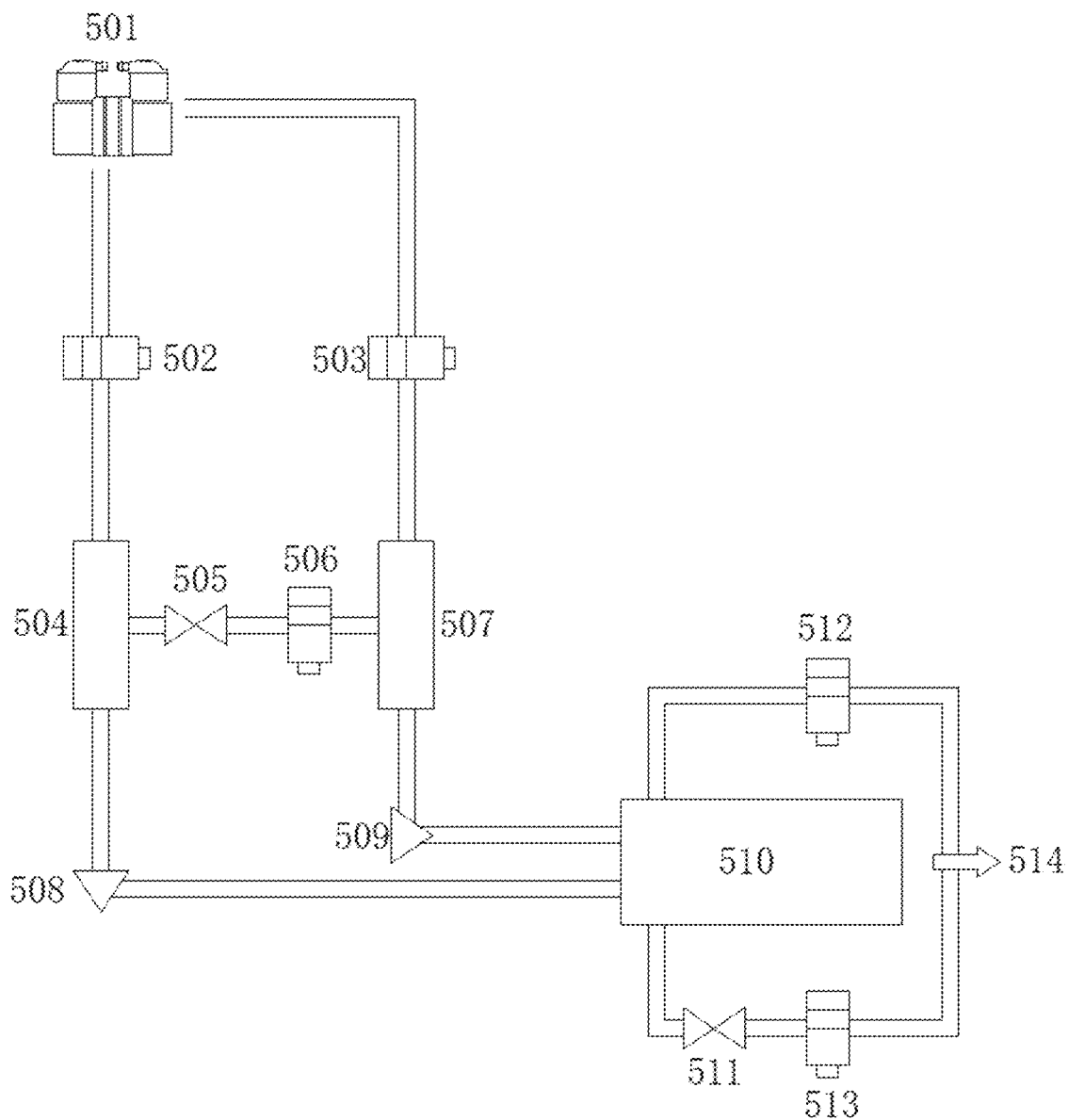
FIG. 5 is a schematic diagram of a control device of an oxygen generator of the present application.
Figure 6:
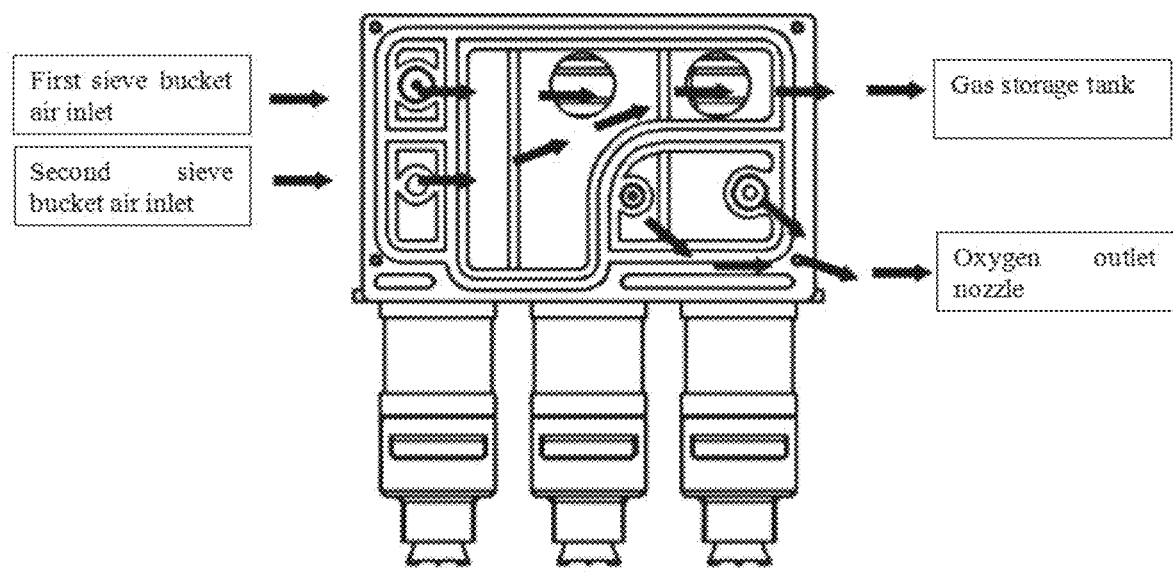
FIG. 6 is a schematic diagram of the oxygen generator of the present application.

As shown in FIG. 5, the application provides a control device of an oxygen generator, including:

an inflating device 501 (air compressor), first solenoid valve 502, second solenoid valve 503, first sieve bucket 504, first oxygen bridge 505, third solenoid valve 506, second sieve bucket 507, first one-way valve 508, second one-way valve 509, gas storage tank 510, second oxygen bridge 511, pulse valve 512, direct current valve 513 and oxygen outlet nozzle 514;

where the inflating device 501 is respectively connected with the first solenoid valve 502 and the second solenoid valve 503 through pipelines, the first sieve bucket 504 is respectively connected with the first solenoid valve 502, the first oxygen bridge 505 and the first one-way valve 508 through pipelines, the second sieve bucket 507 is respectively connected with the second one-way valve 509, the third solenoid valve 506 and the second one-way valve 509 through pipelines, the third solenoid valve 506 is connected with the first oxygen bridge 505 through pipelines, and the gas storage tank is respectively connected with the first one-way valve 508, the second one-way valve 509, the pulse valve 512 and the second oxygen bridge 511 through pipelines, and the second oxygen bridge 511 and the direct current valve 513 are connected through pipelines, and the oxygen outlet nozzle 514 is respectively connected with pulse valve 512 and direct current valve 513 through pipeline.

In one embodiment of the present application, when the oxygen generator is in the direct current oxygen outlet mode, the first solenoid valve 502 is opened when the first sieve bucket 504 discharges nitrogen and closed when oxygen is produced, the second solenoid valve 503 is opened when the second sieve bucket 507 discharges nitrogen and closed when oxygen is produced, the third solenoid valve 506 is opened and the pulse valve 512 is closed. When the oxygen generator is in the pulse oxygen outlet mode, the first solenoid valve 502 is opened when the first sieve bucket 504 discharges nitrogen and closed when oxygen is produced, the second solenoid valve 503 is opened when the second sieve bucket 507 discharges nitrogen and closed when oxygen is produced, the third solenoid valve 506 is opened, the direct current valve 513 is closed and the pulse valve 512 is opened.

The embodiment of the present application has been described above, but the present application is not limited to the above-mentioned specific embodiments, which are only schematic, not restrictive, and ordinary technicians in the field may make many forms under the inspiration of this embodiment, all of which are in the protection of the present application.

What is claimed is:

1. A control method for an oxygen generator, comprising following steps:

step S101, obtaining a first physical sign data of a user according to a first preset time interval A, performing step S102 when the first physical sign data meets one of preset threshold conditions, otherwise performing step S104;

wherein the first physical sign data comprises: blood oxygen saturation, heart rate and breathing frequency;

step S102, switching the oxygen generator to a direct current oxygen outlet mode, and inputting the first physical sign data of the user into a first model, outputting a value as a first opening adjustment value of a direct current oxygen outlet solenoid valve in a first preset time period B;

step S103, adjusting an opening of the direct current oxygen outlet solenoid valve to the first opening adjustment value in the first preset time period B;

step S104, switching the oxygen generator to a pulse oxygen outlet mode, and obtaining a second physical sign data of the user according to a second preset time interval D in a second preset time period C to generate a feature sequence;

the feature sequence comprises N sequence units, and an ith sequence unit represents the second physical sign data of the user at an ith time point, wherein $1 \leq i \leq N$ and $N=C/D$;

the second physical sign data comprises: blood oxygen saturation, heart rate, breathing frequency and respiratory waveform graph;

wherein a horizontal axis of the respiratory waveform graph represents the time point and a vertical axis represents airway pressure;

step S105, inputting the feature sequence into a second model, outputting a value as a second opening adjustment value when a pulse oxygen outlet solenoid valve is opened in a third preset time period E; and step S106, adjusting an opening of the pulse oxygen outlet solenoid valve when opened to the second opening adjustment value in the third preset time period E;

wherein the preset threshold conditions comprise: the blood oxygen saturation is less than a first threshold; the heart rate is greater than or equal to a second threshold value; the breathing frequency is greater than or equal to ta third threshold; wherein the first threshold, the second threshold and the third threshold are all self-defined parameters;

a calculation formula of the first model is as follows:

$$\text{Open}_1 = \frac{1}{W_1} * \text{Blood}^\alpha + W_2 * \text{Heart}^\beta + W_3 * \text{Breath}^\gamma,$$

wherein $\text{Open}_1$ represents the first opening adjustment value, Blood, Heart and Breath respectively represent the blood oxygen saturation, the heart rate and the breathing frequency; $W_1$, $W_2$ and $W_3$ respectively represent a first weight parameter, a second weight parameter and a third weight parameter, $\alpha$, $\beta$, and $\gamma$ respectively represent a first influence coefficient, a second influence coefficient and a third influence coefficient;

the second model comprises N hidden layers, and an ith hidden layer inputs the ith sequence unit of the feature sequence and outputs a hidden state;

the hidden state output by an Nth hidden layer is input into a classifier, and a classification space of the classifier represents the second opening adjustment value when the pulse oxygen outlet solenoid valve is opened in the third preset time period E;

a calculation formula of the second model comprises:

$$r_i = \text{ReLU}(W_i^{r,1} * x_i + W_i^{r,2} * h_{i-1} + b_i^r),$$

$$z_i = \text{ReLU}(W_i^{z,1} * x_i + W_i^{z,2} * h_{i-1} + b_i^z),$$

$$\tilde{h}_1 = \tanh(W_i^{h,1} * x_i + (r_i \odot h_{i-1}) * W_i^{h,2} + b_i^h),$$

$$h_i = z_i \odot h_{i-1} + (1 - z_i) \odot \tilde{h}_1,$$

wherein $X_i$ represents the ith sequence unit of the feature sequence input by the ith hidden layer, and $h_i$ and $h_{i-1}$ respectively represent a hidden state output by the ith hidden layer and an i-1th hidden layer, $h_0$ is assigned as 0, $r_i$, $z_i$ and $\tilde{h}_1$, respectively represent reset gate, update gate and a candidate hidden state of the ith hidden layer, $W_i^r$, $W_i^{r,2}$ and $b_i^r$ respectively represent the first weight parameter, the second weight parameter and an offset parameter corresponding to the reset gate of the ith hidden layer, $W_i^{z,1}$, $W_i^{z,2}$ and $b_i^z$ respectively represent the first weight parameter, the second weight parameter and an offset parameter corresponding to the update gate of the ith hidden layer, $W_i^{h,1}$ $W_i^{h,2}$ and $b_i^h$ respectively represent the first weight parameter, the second weight parameter and the offset parameter corresponding to the candidate hidden state of the ith hidden layer, $\odot$ represents Hadamard product, ReLU represents ReLU activation function, and tanh represents hyperbolic tangent activation function;

obtaining a sample label of a training sample for training the second model comprises following steps:

step S301, before using the oxygen generator, self-defining standard values of the blood oxygen saturation, the heart rate and the breathing frequency of the user as a first vector;

step S302, randomly generating one opening value as the second opening adjustment value when the pulse oxygen outlet solenoid valve is opened in the third preset time period E;

step S303, after the third preset time period E, measuring the blood oxygen saturation, the heart rate and the breathing frequency of the user as a second vector, and calculating a Euclidean distance between the first vector and the second vector;

step S304, repeating the step S301 to the step S303 to obtain the second opening adjustment value corresponding to a minimum value of the Euclidean distance between the first vector and the second vector as the sample label of the training sample; and step S305, repeating the step S304 until sample labels of K training samples are obtained, wherein K is a self-defined parameter.

2. The control method for the oxygen generator according to claim 1, wherein A, β, C, D and E are all self-defined parameters.

3. The control method for the oxygen generator according to claim 1, wherein the first model is fitted by a least square method, and a mean square error is designated as a loss function of the first model; weight parameters and influence coefficients of the first model are updated by a gradient descent algorithm to minimize the loss function of the first model, wherein the first opening adjustment value of a training sample used for fitting the first model is set by evaluating of relevant technical experts.

4. The control method for the oxygen generator according to claim 1, wherein the pulse oxygen outlet solenoid valve is opened at a corresponding time point at a peak of the respiratory waveform graph, and the pulse oxygen outlet solenoid valve is closed at a corresponding time point at a trough of the respiratory waveform graph.

5. A control system of an oxygen generator, using the control method for the oxygen generator according to claim 1, comprising:

a direct current oxygen outlet mode switching module, used for acquiring the first physical sign data of the user according to the first preset time interval A, and switching the oxygen generator to the direct current oxygen outlet mode when the first physical sign data meets one of the preset threshold conditions;

a first opening adjustment value prediction module, used to input the first physical sign data of the user into the first model, to output the value representing the first opening adjustment value of the direct current oxygen outlet solenoid valve in the first preset time period B;

a direct current oxygen outlet solenoid valve adjusting module, used for adjusting the opening of the direct current oxygen outlet solenoid valve to the first opening adjustment value in the first preset time period B;

a pulse oxygen outlet mode switching module, used for acquiring the first physical sign data of the user according to the first preset time interval A, and switching the oxygen generator to the pulse oxygen outlet mode when the first physical sign data does not meet any of the preset threshold conditions;

a second opening adjustment value prediction module, used for acquiring the second physical sign data of the user in the second preset time period C according to the second preset time interval D, generating the feature sequence, inputting the feature sequence into the second model, outputting a value as the second opening adjustment value when the pulse oxygen outlet solenoid valve is opened in the third preset time period E;

a pulse oxygen outlet solenoid valve adjusting module, used for adjusting the opening of the pulse oxygen outlet solenoid valve to the second opening adjustment value in the third preset time period E.

6. A control device of an oxygen generator, using the control method for the oxygen generator according to claim 1, comprising:

an inflating device, a first solenoid valve, a second solenoid valve, a first sieve bucket, a first oxygen bridge, a third solenoid valve, a second sieve bucket, a first one-way valve, a second one-way valve, a gas storage tank, a second oxygen bridge, a pulse valve, a direct current valve and an oxygen outlet nozzle;

wherein the inflating device is respectively connected with the first solenoid valve and the second solenoid valve through pipelines, the first sieve bucket is respectively connected with the first solenoid valve, the first oxygen bridge and the first one-way valve through pipelines, the second sieve bucket is respectively connected with the second one-way valve, the third solenoid valve and the second one-way valve through pipelines, the third solenoid valve is connected with the first oxygen bridge through pipelines, and the gas storage tank is respectively connected with the first one-way valve, the second one-way valve, the pulse valve and the second oxygen bridge through pipelines, and the second oxygen bridge and the direct current valve are connected through pipelines, and the oxygen outlet nozzle is respectively connected with pulse valve and direct current valve through pipeline.

\* \* \* \* \*